US00PP31253P2

(12) United States Plant Patent
van de Pol

(10) Patent No.: US PP31,253 P2
(45) Date of Patent: Dec. 17, 2019

(54) ***CAMPANULA* PLANT NAMED 'PSDBH15701'**

(50) Latin Name: *Campanula poscharskyana*
Varietal Denomination: PSDBH15701

(71) Applicant: Peter van de Pol, Twello (NL)

(72) Inventor: Peter van de Pol, Twello (NL)

(73) Assignee: Genius Genes Production Facilities B.V., Twello (NL)

( * ) Notice: Subject to any disclaimer, the term of this patent is extended or adjusted under 35 U.S.C. 154(b) by 0 days.

(21) Appl. No.: 15/999,928

(22) Filed: Aug. 31, 2018

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
See application file for complete search history.

(56) References Cited

PUBLICATIONS

UPOV hit on *Campanula* plant named, 'PSDBH15701', QZ PBR 20172242, published Dec. 16, 2017.*

* cited by examiner

*Primary Examiner* — Anne Marie Grunberg
(74) *Attorney, Agent, or Firm* — C. A. Whealy

(57) ABSTRACT

A new and distinct *Campanula* plant named 'PSDBH15701', characterized by its compact, upright to spreading and uniformly mounding plant habit; freely flowering habit; dark violet-colored flowers with white-colored centers; and good container and garden performance.

2 Drawing Sheets

Botanical designation: *Campanula poscharskyana.*
Cultivar denomination: 'PSDBH15701'.

BACKGROUND OF THE INVENTION

The present invention relates to a new and distinct *Campanula* plant, botanically known as *Campanula poscharskyana* and hereinafter referred to by the cultivar name 'PSDBH15701'.

The new *Campanula* plant is a product of a planned breeding program conducted by the Inventor in Twello, The Netherlands. The objective of the breeding program is to create new compact and freely-flowering *Campanula* plants with attractive flower colors and good container and garden performance.

The new *Campanula* plant originated from a cross-pollination in August, 2012 of a proprietary selection of *Campanula poscharskyana* identified as code number PSDBH1200302S, not patented, as the female, or seed, parent with a proprietary selection of *Campanula poscharskyana* identified as code number PSDB-1300101S, not patented, as the male, or pollen, parent. The new *Campanula* plant was discovered and selected by the Inventor as a single flowering plant from within the progeny of the stated cross-pollination grown in a controlled greenhouse environment in Twello, The Netherlands in July, 2014.

Asexual reproduction of the new *Campanula* plant by terminal vegetative cuttings in a controlled greenhouse environment in Twello, The Netherlands, since November, 2014, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PSDBH15701'. These characteristics in combination distinguish 'PSDBH15701' as a new and distinct *Campanula* plant:

1. Compact, upright to spreading and uniformly mounding plant habit.
2. Freely flowering habit.
3. Dark violet-colored flowers with white-colored centers.
4. Good container and garden performance.

Plants of the new *Campanula* differ primarily from plants of the female parent selection in flower color as plants of the new *Campanula* have more intense violet-colored flowers with larger white-colored centers.

Plants of the new *Campanula* differ primarily from plants of the male parent selection in the following characteristics:

1. Plants of the new *Campanula* have shorter lateral branches than plants of the male parent selection.
2. Plants of the new *Campanula* and the male parent selection differ in flower color as plants of the new *Campanula* have dark violet-colored flowers with white-colored centers whereas plants of male parent selection have dark purple-colored flowers.

Plants of the new *Campanula* can be compared to plants of *Campanula poscharskyana* 'PSDBH11301', not patented. In side-by-side comparisons conducted in Twello, The Netherlands, plants of the new *Campanula* differ primarily from plants of 'PSDBH11301' in the following characteristics:

1. Plants of the new *Campanula* are more compact than plants of 'PSDBH11301'.
2. Leaves of plants of the new *Campanula* are lighter green in color than leaves of plants of 'PSDBH11301'.
3. Flowers of plants of the new *Campanula* are larger than flowers of plants of 'PSDBH11301'.
4. Flowers of plants of the new *Campanula* have larger white-colored centers than flowers of plants of 'PSDBH11301'.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet is a side perspective view of a typical flowering plant of 'PSDBH15701' grown in a container.

The photograph on the second sheet is a close-up view of a typical flowering plant of 'PSDBH15701'.

DETAILED BOTANICAL DESCRIPTION

Plants used for the aforementioned photographs and following description were grown in 11-cm containers during the summer in a glass-covered greenhouse in Poeldijk, The Netherlands and under cultural practices typical of commercial *Campanula* production. During the production of the plants, day temperatures ranged from 18° C. to 28° C., night temperatures ranged from 14° C. to 20° C. and light levels averaged 6,000 lux. Plants were 13 weeks old when the photographs and description were taken. In the following description, color references are made to The Royal Horticultural Society Colour Chart, 2015 Edition, except where general terms of ordinary dictionary significance are used.

Botanical classification: *Campanula poscharskyana* 'PSDBH15701'.

Parentage:

*Female parent*.—Proprietary selection of *Campanula poscharskyana* identified as code number PSDBH1200302S, not patented.

*Male parent*.—Proprietary selection of *Campanula poscharskyana* identified as code number PSDB-1300101S, not patented.

Propagation:

*Type*.—By terminal vegetative cuttings.

*Time to initiate roots, summer*.—About seven to ten days at temperatures about 23° to 24° C.

*Time to initiate roots, winter*.—About ten to twelve days at temperatures about 22° to 23° C.

*Time to produce a rooted young plant, summer*.—About 36 days at temperatures about 23° to 24° C.

*Time to produce a rooted young plant, winter*.—About 42 days at temperatures about 22° to 23° C.

*Root description*.—Fine, fleshy; typically white in color, actual color of the roots is dependent on substrate composition, water quality, fertilizers, substrate temperature and physiological age of roots.

*Rooting habit*.—Moderately freely branching; medium density.

Plant description:

*Plant and growth habit*.—Herbaceous perennial; compact, upright to spreading and uniformly mounding plant habit; flattened globular in shape; moderately vigorous growth habit; moderate growth rate; numerous campanulate flowers positioned above and beyond the foliar plane.

*Plant height, soil level to top of foliar plane*.—About 16.2 cm.

*Plant height, soil level to top of floral plane*.—About 18.4 cm.

*Plant width*.—About 41.9 cm.

*Lateral branch description*.—Branching habit: Freely branching habit with about 48 lateral branches developing per plant. Length (excluding inflorescences): About 15.9 cm. Diameter: About 2.5 mm. Internode length: About 1.6 cm. Strength: Moderately strong. Aspect: Upright to horizontal. Texture and luster: Smooth, glabrous; glossy. Color, developing: Close to 144B. Color, developed: Close to 146D.

Leaf description:

*Arrangement*.—Alternate, simple.

*Length*.—About 2.8 cm.

*Width*.—About 3 cm.

*Shape*.—Deltoid to reniform.

*Apex*.—Broadly and bluntly acute.

*Base*.—Developing leaves, broadly attenuate; developed leaves, cordate.

*Margin*.—Coarsely and irregularly dentate.

*Texture and luster, upper and lower surfaces*.—Smooth, glabrous; slightly glossy.

*Venation pattern*.—Pinnate.

*Color*.—Developing leaves, upper surface: Close to between 137C and 143A. Developing leaves, lower surface: Close to 138B. Fully expanded leaves, upper surface: Close to 137B; venation, close to 145A. Fully expanded leaves, lower surface: Close to 138B; venation, close to 145B.

*Petioles*.—Length: About 3.2 cm. Diameter: About 1 mm by 1.5 mm. Strength: Low. Texture and luster, upper and lower surfaces: Smooth, glabrous; glossy. Color, upper surface: Close to 145C; margins, close to 144A. Color, lower surface: Close to 145B.

Flower description:

*Flower arrangement and flowering habit*.—Single campanulate flowers arranged in terminal and axillary simple cymes; flowers face mostly upright to outwardly; freely flowering habit with about 2,500 flowers develop per plant during the flowering season.

*Natural flowering season*.—Plants begin flowering about ten weeks after planting; relatively long flowering period, plants flower continuously from the spring into the autumn in The Netherlands.

*Flower longevity on the plant*.—About ten days; flowers persistent.

*Fragrance*.—Faint; slightly moldy.

*Flower buds*.—Length: About 8 mm. Diameter: About 1.3 cm. Shape: Oblong. Texture and luster: Smooth, glabrous; glossy. Color: Close to 91B to 91C; fading towards the base to close to 91D and 145D.

*Inflorescence height*.—About 3.3 cm.

*Inflorescence diameter*.—About 3.5 cm.

*Flower diameter*.—About 1.2 cm.

*Flower depth (height)*.—About 2.5 cm.

*Petals*.—Quantity and arrangement: Typically five per flower, arranged in a single whorl; lower 30% of the petal is fused. Length: About 1.4 cm. Width: About 6 mm. Shape: Obovate; free parts, slightly recurved. Apex: Acute. Margin: Entire; not undulate. Texture and luster, upper surface: Smooth, glabrous; slightly velvety; matte. Texture and luster, lower surface: Smooth, glabrous; slightly glossy. Color: When opening, upper surface: Close to between 86C and N87B; towards the throat and throat, close to NN155D. When opening, lower surface: Close to between N87D and N88D; towards the tube and tube, close to NN155D. Fully opened, upper surface: Close to between N87A and N88A; towards the throat and throat, close to NN155D; venation, similar to lamina colors; colors do not change with development. Fully opened, lower surface: Close to N88C; towards the tube and tube, close to NN155D; venation, similar to lamina colors; colors do not change with development.

*Sepals*.—Quantity and arrangement: Typically five per flower, arranged in a single whorl. Length: About 7 mm. Width: About 2 mm. Shape: Lanceolate. Apex: Acute. Base: Broadly cuneate. Margin: Entire. Texture and luster, upper and lower surfaces: Smooth, glabrous; slightly glossy. Color: When opening and fully opened, upper surface: Close to 143B. When opening and fully opened, lower surface: Close to 138B.

*Peduncles*.—Length: About 3.2 cm. Diameter: About 1 mm. Aspect, flowers in terminal inflorescences: Mostly upright. Aspect, flowers in axillary inflorescences: About 30° from lateral branch axis. Strength: Moderately strong. Texture and luster: Smooth, glabrous; glossy. Color: Close to 144C.

*Pedicels*.—Length: About 1.1 cm. Diameter: About 0.75 mm. Aspect: About 30° from peduncle axis. Strength: Moderately strong. Texture and luster: Smooth, glabrous; moderately glossy. Color: Close to 144C.

*Reproductive organs*.—Stamens: Quantity: Typically five per flower. Filament length: About 1.5 mm. Filament color: Close to NN155D. Anther length: About 3 mm. Anther diameter: About 0.2 mm. Anther shape: Narrowly oblong. Anther color: Close to 11D. Pollen amount: Scarce to moderate. Pollen color: Close to 4D. Pistils: Quantity per flower: One. Pistil length: About 8 mm. Style length: About 6.5 mm. Style color: Close to NN155B. Stigma diameter: About 2.5 mm. Stigma shape: Three-parted, decurrent. Stigma color: Close to 91C to 91D. Ovary color: Close to 143C.

*Seeds and fruits*.—To date, seed and fruit development has not been observed on plants of the new *Campanula*.

Pathogen & pest resistance: To date, plants of the new *Campanula* have not been noted to be resistant to pathogens and pests common to *Campanula* plants.

Garden performance: Plants of the new *Campanula* have exhibited good garden performance and to tolerant to rain, wind, high temperatures about 35° C. and to be suitable for USDA Hardiness Zones 3 to 9.

It is claimed:

1. A new and distinct *Campanula* plant named 'PSDBH15701' as illustrated and described.

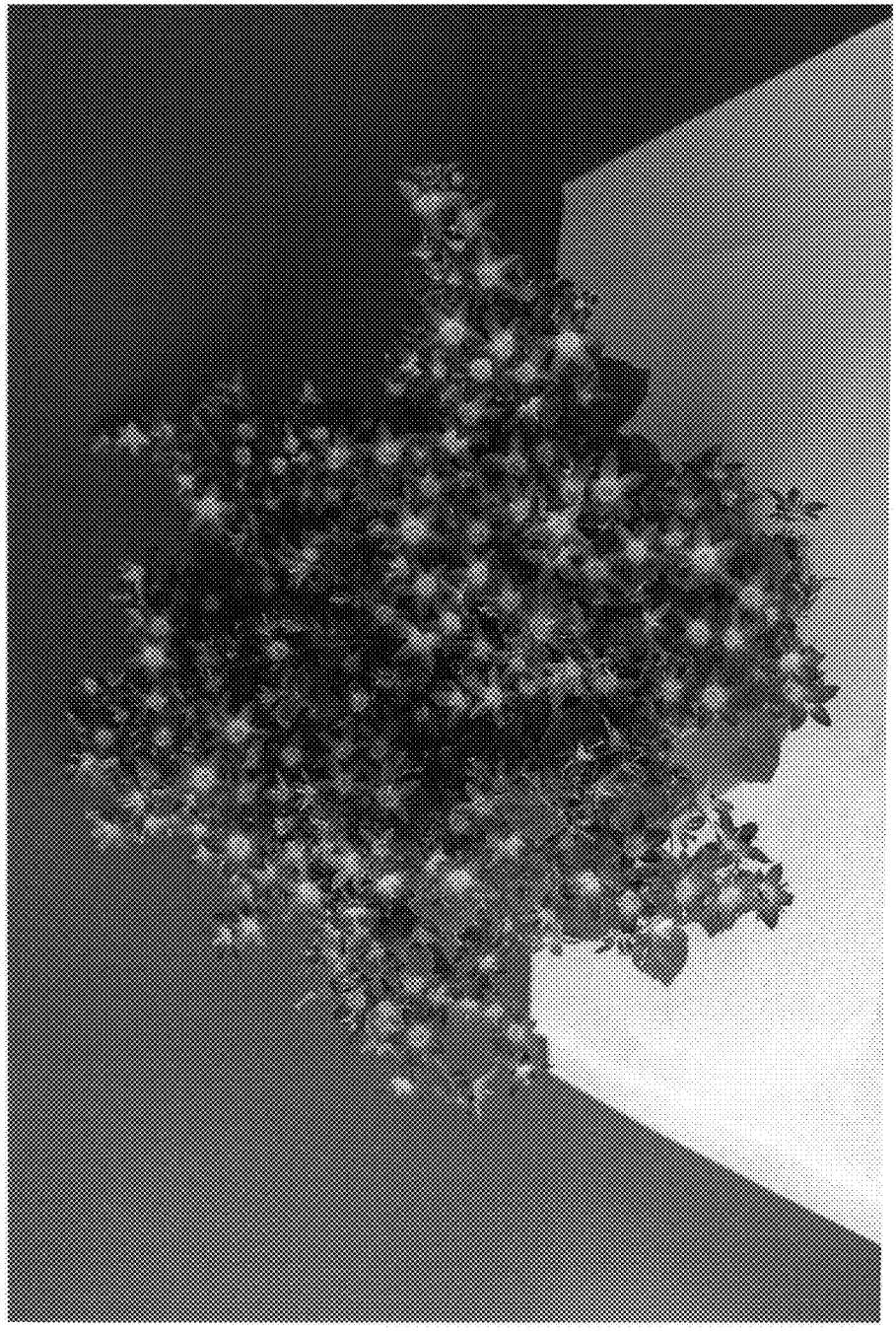

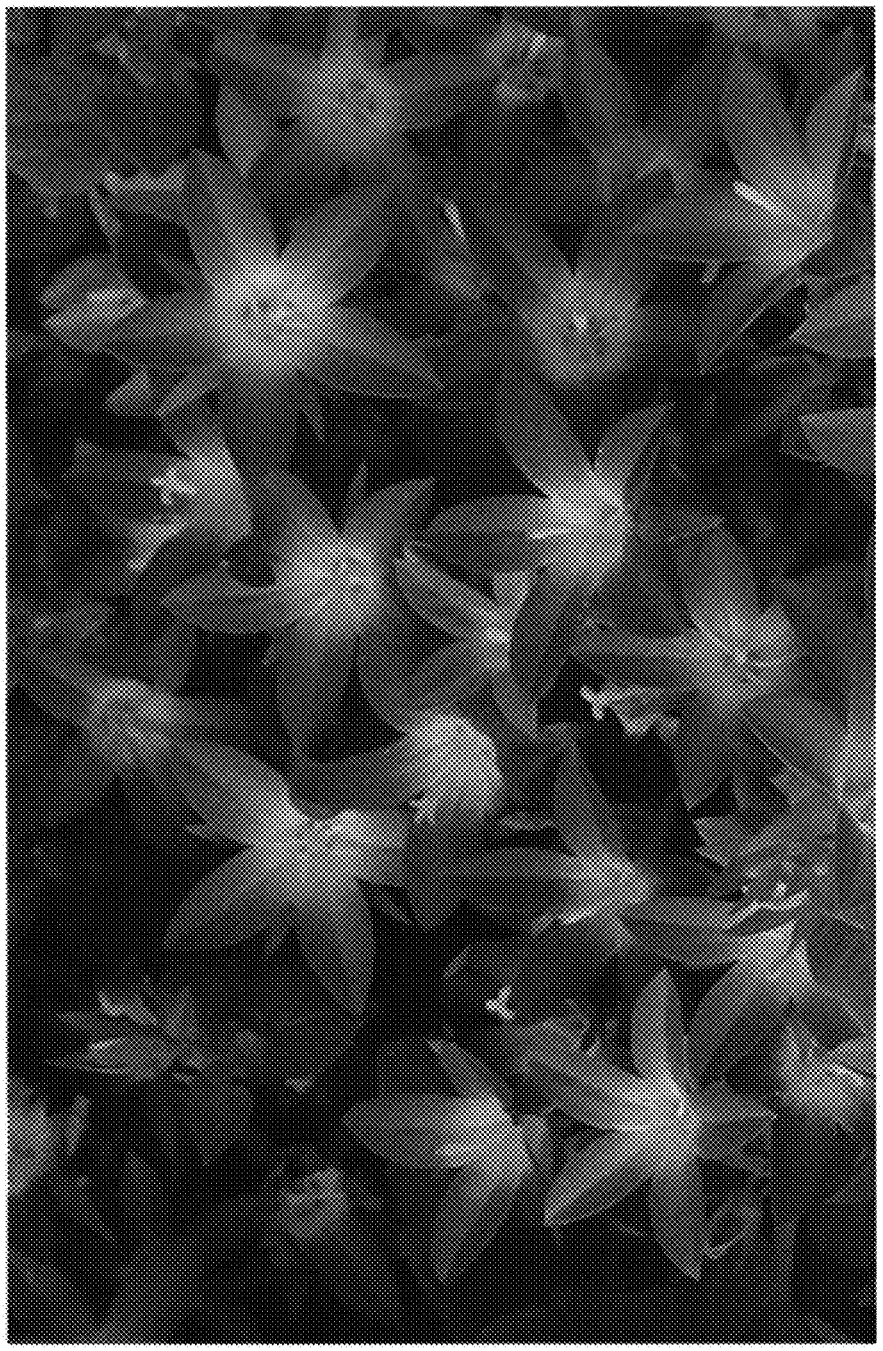

* * * * *